United States Patent
Kraemer et al.

(10) Patent No.: US 9,915,672 B2
(45) Date of Patent: *Mar. 13, 2018

(54) AUTOMATIC ANALYZER

(71) Applicants: Roche Diagnostics Operations, Inc., Indianapolis, IN (US); Hitachi High-Technologies Corporation, Minato-ku (JP)

(72) Inventors: Reinhold Kraemer, Peissenberg (DE); Susumu Sakairi, Hitachinaka (JP); Stephan Sattler, Starnberg (DE); Katsuaki Takahashi, Hitachinaka (JP)

(73) Assignees: Roche Diagnostics Operations, Inc., Indianapolis, IN (US); Hitachi High-Technologies Corporation, Tokyo (JP)

( * ) Notice: Subject to any disclaimer, the term of this patent is extended or adjusted under 35 U.S.C. 154(b) by 240 days.

This patent is subject to a terminal disclaimer.

(21) Appl. No.: 14/994,575

(22) Filed: Jan. 13, 2016

(65) Prior Publication Data

US 2016/0124008 A1    May 5, 2016

Related U.S. Application Data

(63) Continuation of application No. 13/360,202, filed on Jan. 27, 2012, now Pat. No. 9,274,133, which is a
(Continued)

(30) Foreign Application Priority Data

Jul. 29, 2009 (JP) ................................ 2009-176005
Dec. 14, 2009 (EP) .................................... 09179068

(51) Int. Cl.
*G01N 35/02* (2006.01)
*G01N 35/04* (2006.01)
(Continued)

(52) U.S. Cl.
CPC ....... *G01N 35/025* (2013.01); *G01N 35/0099* (2013.01); *G01N 35/04* (2013.01);
(Continued)

(58) Field of Classification Search
CPC ........................... G01N 35/10; G01N 35/4055
See application file for complete search history.

(56) References Cited

U.S. PATENT DOCUMENTS

| 4,699,766 A | 10/1987 | Yamashita |
| 5,183,638 A | 2/1993 | Wakatake |

(Continued)

FOREIGN PATENT DOCUMENTS

| EP | 1225450 A1 | 7/2002 |
| EP | 703457 B1 | 12/2004 |

(Continued)

OTHER PUBLICATIONS

European Search Report dated Jul. 27, 2010 in Application No. EP09179068, 2 pages.
(Continued)

*Primary Examiner* — Jill A Warden
*Assistant Examiner* — Matthew D Krcha
(74) *Attorney, Agent, or Firm* — Woodard, Emhardt, Moriarty, McNett & Henry LLP

(57) ABSTRACT

According to an embodiment of the disclosure, the analyzer includes a reagent driving disk that accommodates a reagent configured for analysis and that transports the reagent to a desired position, and a fixed disk that has a reagent stand-by position in which to make a reagent container containing the reagent, temporarily stand by, and a magnetic particles stirring position for stirring magnetic particles. A portion of the reagent stand-by position is constituted by a loading system. A reagent container moving unit moves reagent containers containing the reagent, between the reagent driv-
(Continued)

ing unit and the fixed disk, according to analytical request status. Providing in a part of the fixed disk the loading system constructed so that reagent containers containing the reagent can be mounted therein during operation enables changing of reagent containers, irrespective of an operational status of the reagent driving disk, and the system to having cold-storage functionality.

15 Claims, 12 Drawing Sheets

Related U.S. Application Data continuation of application No. PCT/EP2010/060977, filed on Jul. 28, 2010.

(51) Int. Cl.
    *G01N 35/10*     (2006.01)
    *G01N 35/00*     (2006.01)

(52) U.S. Cl.
    CPC ......... *G01N 35/10* (2013.01); *G01N 35/1002* (2013.01); *G01N 2035/00435* (2013.01); *G01N 2035/00524* (2013.01); *G01N 2035/00534* (2013.01); *G01N 2035/0425* (2013.01); *G01N 2035/0443* (2013.01); *G01N 2035/0453* (2013.01); *G01N 2035/0455* (2013.01); *G01N 2035/0465* (2013.01); *Y10T 436/11* (2015.01); *Y10T 436/114165* (2015.01)

(56) References Cited

U.S. PATENT DOCUMENTS

| | | |
|---|---|---|
| 5,324,635 A | 6/1994 | Kawase et al. |
| 5,360,597 A | 11/1994 | Jakubowicz |
| 5,578,269 A | 11/1996 | Yaremko et al. |
| 5,827,479 A | 10/1998 | Yamazaki et al. |
| 6,599,473 B1 | 7/2003 | Egger et al. |
| 7,384,601 B2 | 6/2008 | Matsubara et al. |
| 7,547,414 B2 | 6/2009 | Nishida |
| 7,749,441 B2 | 7/2010 | Hanawa et al. |
| 2004/0057872 A1 | 3/2004 | Shibuya et al. |
| 2005/0013735 A1 | 1/2005 | Gebrian et al. |
| 2006/0062692 A1 | 3/2006 | Tokieda et al. |
| 2006/0104862 A1 | 5/2006 | Pages Pinyol |
| 2007/0128085 A1 | 6/2007 | Burkhardt et al. |
| 2008/0199358 A1 | 8/2008 | Yamano |

FOREIGN PATENT DOCUMENTS

| | | |
|---|---|---|
| EP | 1051621 B1 | 4/2005 |
| EP | 1275966 B1 | 7/2006 |
| JP | 4033060 B2 | 1/2008 |

OTHER PUBLICATIONS

International Search Report dated Nov. 29, 2010 in Application No. PCT/EP2010/060977, 3 pages.

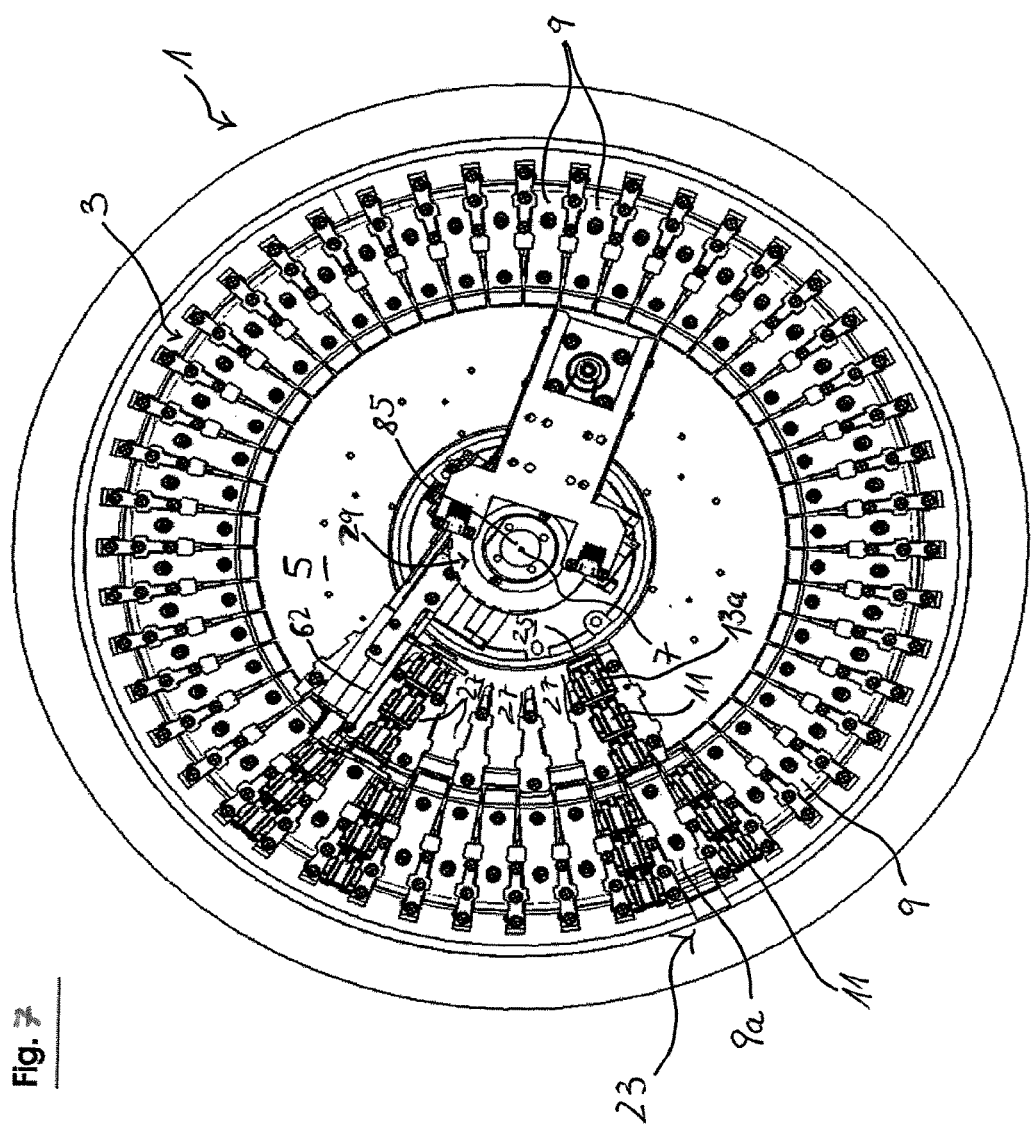

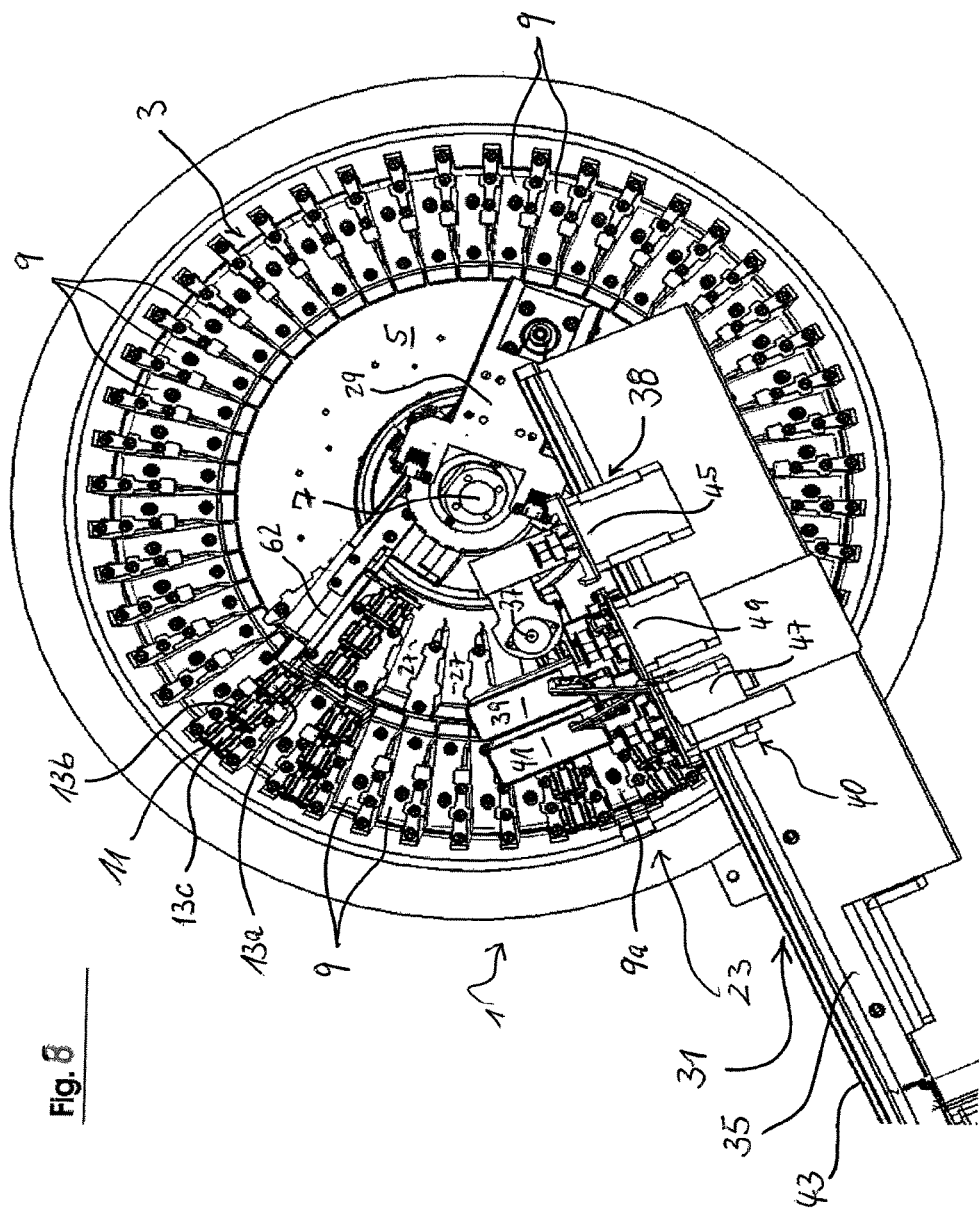

Fig. 9a
Fig. 9b
Fig. 10

AUTOMATIC ANALYZER

CROSS-REFERENCE TO RELATED APPLICATIONS

This application is a continuation of U.S. Continuation application Ser. No. 13/360,202, filed 27 Jan. 2012 which is a continuation of International Application No. PCT/EP2010/060977, filed 28 Jul. 2010, which claims the benefit of Japanese Patent Application No. 2009-176005, filed 29 Jul. 2009, and European Patent Application No. 09179068.3, filed 14 Dec. 2009, the disclosures of which are hereby incorporated by reference in their entirety.

TECHNICAL FIELD

The present invention relates generally to automatic analyzers that conduct qualitative/quantitative analyses on biological samples such as blood and urine. More particularly and with regard to a first aspect, the invention concerns an automatic analyzer including a reagent container holding unit that holds reagent containers each containing a reagent to be used for analysis, and a reagent container supply unit that supplies reagent containers to the reagent container holding unit.

BACKGROUND

Automatic analyzers that analyze blood and other biological samples automatically and output the results are among the apparatuses absolutely necessary to perform efficient analyses at the testing centers and other medical laboratory facilities that subcontract to test/examine samples on behalf of hospitals and clinics that have many patients. It is being desired that these automatic analyzers be more compact, capable of conducting more kinds of analyses, and have higher throughput.

If the reagent set up in the apparatus runs short during analysis, stopping the analysis before taking any necessary steps will reduce the efficiency of the analysis. Automatic analyzers are therefore designed so that if a shortage of reagent is likely, the apparatus will warn the operator about the shortage, thus avoiding the situation that the operator will have to stop the apparatus to replace the reagent with a new one of the same kind during the analysis.

JP 4033060 describes a more advanced technique for preventing a shortage of reagent from occurring during analysis. In the technique of JP 4033060, a first and a second reagent-container storage means are provided beforehand and if the reagent stored within the first reagent-container storage means runs short, a reagent container as a replacement is supplied from the second reagent-container storage means automatically.

According to the technique described in JP 4033060, although a plurality of reagent containers can be stored in the second reagent-container storage means, one reagent container can only be conveyed at a time from the second reagent-container storage means to the first reagent-container storage means. In addition, holding a plurality of reagent containers in the second reagent-container storage means for an extended time requires providing cold-storage means, the provision of which could result in an oversized apparatus structure.

Analyzers are known in various embodiments, e.g., from EP 0 703 457 B1, EP 1 275 966 B1, U.S. Pat. No. 7,547,414 B2 and U.S. Pat. No. 7,384,601 B2.

Those analyzers are used for automatically analyzing samples in order to determine the existence and particularly the concentration of specific components in the samples. Such analyzers are widely used in hospitals and clinical laboratories to analyze biological samples, namely body fluids collected from patients, such as blood and urine, in order to diagnose their morbidities.

A method for analyzing such a biological fluid sample by means of an analyzer of the above mentioned type is explained in, e.g., EP 1 051 621 B1.

The workflow of an analyzer of the above mentioned kind is usually completely sample orientated, i.e., analytical determinations are performed serially in a respective fluid sample, wherein for each analytical determination a set of different reagents is used to be added to a separated part of said sample. It is therefore required to provide a lot of different reagents on the turntable of the apparatus for providing reagents, and it is required that a fast access to particular reagent container assemblies on the turntable by treatment means such as pipetting means or agitating means is possible in order to achieve a high throughput of the analyzer. It is generally required that such an analyzer apparatus and particularly the apparatus for providing reagents has small dimensions to be space-saving.

SUMMARY

It is against the above background that the embodiments of the present disclosure provide certain unobvious advantages and advancements over the prior art. In particular, the inventor(s) have/has recognized a need for improvements in automatic analyzers.

Although the embodiments of the present disclosure are not limited to specific advantages or functionality, it is noted that in a first aspect, the present disclosure provides an automatic analyzer that enables automatic replacement of a reagent during analysis and eliminates a need of providing such reagent cold-storage means as described in Patent JP 4033060.

According to a second aspect, the present disclosure relates to an analyzer comprising an apparatus for providing reagents to be used in analyses to be performed by the analyzer,
wherein said apparatus for providing reagents comprises
a turntable having an axis of rotation and being adapted for storing thereon a plurality of reagent container assemblies in an arrangement of at least one arcuate row,
at least one treatment zone for treating reagent container assemblies stored on said turntable, and
treatment means for treating reagent container assemblies positioned in said treatment zone,
wherein said turntable comprises compartments arranged to accommodate the reagent container assemblies at predetermined locations on the turntable so as to form said arrangement of at least one arcuate row of reagent container assemblies corresponding to the arrangement of said compartments, and wherein said turntable is adjustable by rotation so as to selectively move compartments in predetermined positions for disposing reagent container assemblies in predetermined positions in said treatment zone.

As to the second aspect of the invention it is an object of the present invention to provide an analyzer of the above mentioned type with an apparatus for providing reagents that may be operated in a more efficient way in comparison with analyzers of the prior art.

In order to attain the first above mentioned object, an automatic analyzer according to the first aspect of the present invention is configured as follows:

The analyzer includes: a reagent container transport unit adapted for mounting a plurality of reagent containers thereon, and constructed to transport the reagent containers to desired positions; a reagent container mounting unit adjacent to the reagent container transport unit and having an ability to supply the reagent containers to the reagent container transport unit; and a reagent container moving unit that moves the reagent containers from the reagent container mounting unit to the reagent container transport unit.

A more preferred aspect of the present invention is outlined below.

Only a reagent driving disk that moves to positions for reagent dispensing and stirring, reagent container lid opening/closing, and the like, is provided as a disk in the automatic analyzer according to an aspect of the present invention. In an automatic analyzer according to a more preferred aspect of the present invention, however, a fixed disk without a drive such as a motor is added at a location adjacent to such a reagent driving disk. The automatic analyzer according to the more preferred aspect also includes a magnetic particles stirring unit at a position adjacent to the fixed disk. This layout of the fixed disk and the magnetic particles stirring unit enables a temporarily idle reagent container on the fixed disk to be made to stand by thereon. Thus, the reagent driving disk is of compact construction. Additionally, positioning the magnetic particles stirring unit adjacently to the fixed disk renders magnetic particles stirring executable on the fixed disk, ensures a sufficient stirring time, and enables uniform stirring without causing unfavorable events such as bubbling. Furthermore, a reagent can be dispensed into a reagent container on the fixed disk as well as on the driving disk, so that magnetic particles in a reagent in one reagent container can be stirred on the fixed disk while a reagent in other reagent container can be dispensed on the fixed disk.

A reagent container moving unit adapted to move reagent containers between the reagent driving disk and the fixed disk is further provided, whereby the reagent containers can be moved between the reagent driving disk and the fixed disk according to a particular analytical situation.

Moreover, providing a loading system in a part of the reagent stand-by disk enables reagent container replacement, even during reagent transport disk operation. The reagent can therefore be replaced without reducing throughput. Since a cooling function for the loading system is further added and since the cooling function is provided in a part of the reagent disk, the loading system can be provided without adding a space in any other section of the apparatus. As a result, the reagent disk alone can be miniaturized and the apparatus correspondingly downsized.

The following advantageous effects of the invention may be indicated:
(1) A large number of reagent containers including the one standing by can be set in the apparatus.
(2) The number of reagent containers changes can be reduced.
(3) The reagent disk can be miniaturized.
(4) The reagent containers can be replaced without reducing throughput.

According to the second aspect of the present invention the analyzer of the above mentioned kind is characterized in that said turntable comprises a first circular turntable partition centered around the axis of rotation and carrying said arcuate row of compartments, and a second turntable partition arranged radially adjacent to said first turntable partition and carrying a first compartment for accommodating a reagent container assembly therein, wherein said first turntable partition is rotatable relative to the second turntable partition about said axis of rotation so as to selectively adjust a compartment of said first turntable partition in radial alignment with said first compartment of the second turntable partition in a mutual transfer position in which a reagent container assembly is radially shiftable between said aligned compartments in said treatment zone.

The analyzer according to the present invention allows to pursue a specific strategy in supplying the reagents required for performing the analytical determinations according to specific assay protocols.

The steps of extracting different reagents from reagent container assemblies may take different times, depending on the particular reagents and special preparation measures to be taken before particular reagents can be withdrawn from reagent container assemblies by way of pipetting. Such a preliminary preparation step is a mixing or agitating step which is necessary to homogenize reagents which tend to sediment. One example for such a reagent is a suspension of beads. Such a suspension of beads is typically used in almost each analytical determination process to be performed with an analyzer according to the present invention. The beads tend to deposit on the bottom of the container section which includes the bead suspension. If beads of such a sedimented suspension are required for a present analytical determination process it is necessary to homogenize the suspension by way of agitation with a stirrer or the like which is to be dipped into the reagent container section. Such an agitating or mixing step is comparatively time-consuming.

According to the present invention such a time-consuming mixing step may be performed with the particular reagent to be mixed being provided in a reagent container assembly that is temporarily stored in the first compartment of the second turntable partition during the mixing step. In the meantime the first turntable partition may be operated to provide other reagent container assemblies in the treatment zone in order to be treated on a faster time scale, e.g., by extracting reagents therefrom by means of pipetting units. In other words, in the part of the treatment zone which is supplied with reagent container assemblies by the first turntable partition, treatment steps may be performed independently and parallel to a treatment step performed in the part of the treatment zone which is assigned to the second turntable partition.

After the termination of a time-consuming treatment step performed on a reagent container assembly provided on the second turntable partition, that reagent container assembly may be transferred to the first turntable partition. Thereafter, a further reagent container assembly may be transferred from the first turntable partition to the second turntable partition when the respective compartments have been radially aligned in their mutual transfer position.

The operation of the turntable and the treatment means is controlled by a controller in a time-optimized manner.

Preferably, the first circular turntable partition is arranged radially outward of the second circular turntable partition with regard to the axis of rotation. Such an arrangement can be realized in a space-saving manner with a relatively great capacity of the first turntable partition for storing a great number of reagent container assemblies.

The reagent container assemblies to be used in the analyzer according to the present invention are preferably multisection containers with at least two, preferably three container sections, each of which has an inner volume containing a particular reagent. The container sections are arranged side-by-side in a row and are connected to form a unitary cassette type assembly which has upper openings for gaining access to the inner volumes of the container sections by a stirrer, a pipetting unit or the like. Each opening is normally closed and covered by a respective cap which can be reversibly moved from its closing cover position to an opening position. Usually a cap will be in the opening position only for short times during momentary phases of access to the inner volume of the respective container section. Thereafter the cap should be moved back in the closing position in order to avoid evaporation and/or contamination of the reagent in the container section.

The analyzer according to the present invention preferably comprises a cap manipulating mechanism for selectively displacing caps of reagent container sections into their opening position and closing position respectively. The cap manipulating mechanism is a part of the treating means of the analyzer.

In order to enable an automatic shifting of a reagent container assembly between the first turntable partition and the second turntable partition the analyzer of the present invention preferably comprises a container shift mechanism for shifting reagent container assemblies between radially aligned compartments of said turntable partitions in their mutual transfer positions, wherein said container shift mechanism comprises radially movable engagement means for engaging and shifting a reagent container assembly between compartments in their mutual transfer position. Such a shifting of a reagent container assembly is enabled only in the case that one of the aligned compartments is vacant.

According to a preferred embodiment of the invention the second turntable partition carries a plurality of compartments including said first compartment for accommodating reagent container assemblies in an arrangement of an arcuate row radially adjacent said arcuate row of compartments of the first turntable partition, wherein at least two of the compartments, preferably all compartments of said second turntable partition are radially alignable with respective compartments of the first turntable partition in mutual transfer positions. With regard to the last mentioned embodiment of the invention it is preferred that said container shift mechanism is movable around the axis of rotation in selected angular positions corresponding to angular positions of the radial alignment of compartments aligned in their mutual transfer positions. In this manner it is possible to exchange reagent container assemblies between various compartments of the turntable partitions. The compartments of the second turntable partitions may be used to store backup reagent container assemblies containing reagents which are used in larger amounts than other reagents for analytical determinations to be performed according to predetermined assay protocols. Such a backup reagent container assembly may be transferred from the second turntable partition to the first turntable partition in exchange with an at least partially empty reagent container assembly. In order to enable such transfers of reagent container assemblies between the turntable partitions it is necessary that at least one compartment is vacant for accommodating a reagent container assembly. The analyzer according to the present invention preferably comprises as treatment means pipetting means which are movable for access to at least one of reagent container assemblies positioned in said predetermined positions in said treatment zone. The pipetting means should be movable for access to reagent container assemblies positioned on the first turntable section and provided in said treatment zone. According to a further embodiment of the invention the pipetting means are also movable for access to a reagent container assembly positioned on the second turntable partition and provided in said treatment zone.

Preferably one of the compartments of the first turntable partition and at least one of the compartments of the second turntable partition are radially aligned to dispose reagent container assemblies contained therein on a straight radial line when positioned relative to each other in said predetermined positions in the treatment zone, wherein said apparatus for providing reagents comprises a driving and guiding means for selectively moving said pipetting means to reagent container assemblies positioned relative to each other in said predetermined positions in the treatment zone.

According to a further preferred embodiment of the invention said pipetting means comprise at least two pipetting units wherein said driving and guiding means are adapted to selectively move each pipetting unit according to a specific treatment program. The pipetting units may be guided for common movement along a linear guidance which is oriented in the radial direction of the turntable. Each pipetting unit has a pipette tip or intake tube and the distance between the pipette tips of the common horizontally movable pipette units correspond to the distance between the centers of openings of adjacent reagent container sections of a reagent container assembly so that both pipette tips may be simultaneously moved into adjacent openings of a reagent container assembly positioned in the treatment zone. For the up-and-down movement of the pipette tips vertical drive means are provided which are preferably controllable to drive the pipetting tips independently from each other.

As mentioned above, it is preferred that the treatment means comprise agitating means including a stirrer adapted to access a reagent container assembly accommodated in the first compartment of the second turntable partition.

In case that the container shift mechanism is adapted to be operated in different angular positions beside or outside of the treatment zone section, in which the pipetting means operates, it is preferred that the container shift mechanism and the pipetting means and the agitating means are selectively operable in order to simultaneously treat separate reagent container assemblies with the container shift mechanism, the pipetting means and the agitating means, respectively.

The agitating means and the pipetting means are simultaneously operable in order to simultaneously treat separate reagent container assemblies, or in special cases the same reagent container assembly, with the agitating means and the pipetting means.

It is in the frame of the present invention that the first turntable partition and the second turntable partition are both rotatable about the axis of rotation in order to place reagent containers in predetermined positions. However, according to a preferred embodiment of the invention the second turntable partition is fixed with regard to the axis of rotation, whereas the first turntable partition is rotatable around the second turntable partition.

According to a further preferred embodiment of the invention the turntable has a radial inner center including the axis of rotation, wherein a cleaning station for cleaning treatment means and a drain channel for draining cleaning fluid is arranged in the area of said radial inner center. Such a construction may be realized by means of a hollow shaft of the turntable and at least one cleaning fluid source, particularly a nozzle providing cleaning fluid to be drained off in the drain channel. Since a stirrer of the agitating means usually must be cleaned after each mixing operation it is preferred that said agitating means is movable between a working position to agitate fluid in a reagent container assembly positioned in a compartment of the second turntable partition, particularly in the first compartment thereof, and a cleaning position to be cleaned by said cleaning means of said cleaning station.

These and other features and advantages of the embodiments of the present invention will be more fully understood from the following detailed description taken together with the accompanying claims. It is noted that the scope of the claims is defined by the recitations therein and not by specific discussion of features and advantages set forth in the present description.

BRIEF DESCRIPTION OF THE DRAWINGS

The following detailed description of the embodiments of the present invention can be best understood when read in conjunction with the following drawings, where like structure is indicated with like reference numerals and in which:

FIG. 3-1 is a perspective view of the reagent disk, showing the disk particularly with a lid removed;

FIG. 3-2 is a top view of the reagent disk, showing the disk particularly with the lid removed;

FIG. 3-3 is a perspective view of the reagent disk, showing the disk particularly under the state thereof in FIG. 3-2;

FIG. 5-1 is a schematic view showing a part of the reagent container moving unit.

FIG. 7 is a top plan view of an embodiment of a turntable of an analyzer according to the second aspect of the present invention;

FIG. 8 is a top plan view of an apparatus for providing reagents according to the present invention including the turntable of FIG. 7;

FIG. 9a and FIG. 9b are perspective views of a reagent container assembly in the closed state and in the opened state;

FIG. 10 is a side view of treatment means of the apparatus of FIG. 8;

Figure 1:
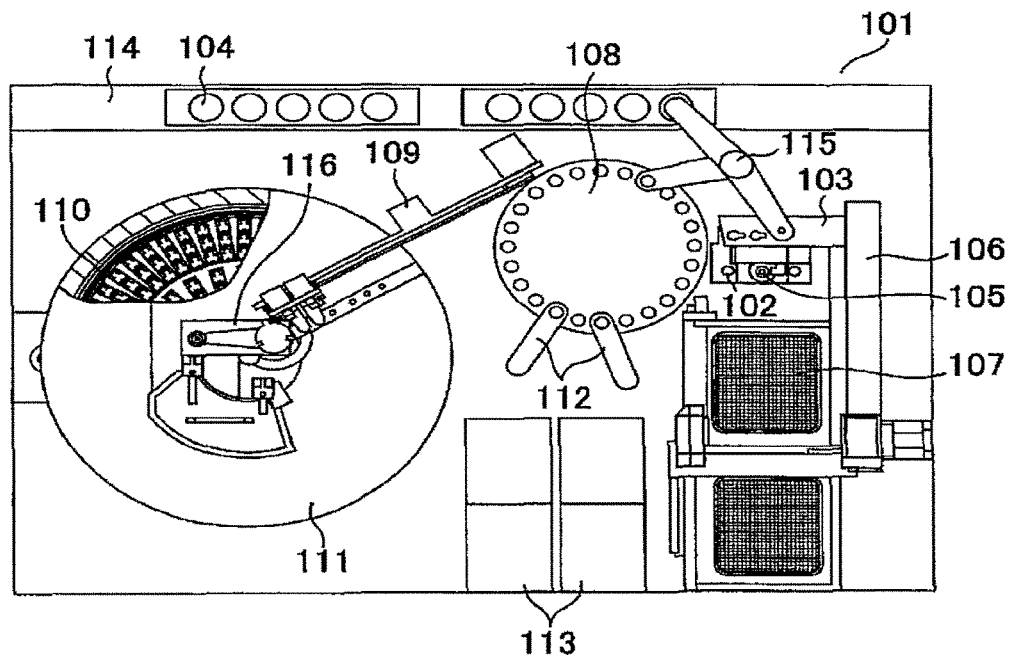
FIG. 1 is a total apparatus configuration diagram of an automatic analyzer of the present invention, the analyzer including a reagent disk which is hereinafter also called turntable.

Reference Numerals of the first embodiment according to the first aspect of the invention.

101 Automatic analyzer
102 Sample dispensing tip reaction vessel disposal hole
103 Sample dispensing tip buffer
104 Sample
105 Reaction solution stirring unit
106 Sample dispensing tip reaction vessel transport unit
107 Sample dispensing tip reaction vessel
108 Incubator disk
109 Reagent dispensing pipettor
110 Reagent container
111 Reagent disk
112 Reaction solution suction nozzle
113 Detection unit
114 Sample transport line
115 Sample dispensing unit
116 Magnetic particles stirring arm
201 Lid
202 Jacket
205 Loading system
301 Reagent driving disk
302 Reagent driving disk driving unit
303 Fixed disk
304 Loading system
305 Reagent container moving unit
306 Reagent information reading device
307 Partition plate
308 Reagent stand-by position
309 Reagent stirring position
310 Reagent dispensing position
401 Reagent placing unit
402 Reagent actuator
403 Indicator
404 Loading system locking unit
405 Indicator lamp
501 Arm mechanism
502 Drive portion
503 Arm
504 Lateral arm drive portion
505 Rotational arm drive portion
601 Analysis request process
602 Confirmation process whether a reagent to be used for an analysis on a reagent driving disk
603 Process for no reagent movement
604 Confirmation process whether a vacant position presents in a reagent driving disk or not
605 Process for moving a reagent container from a fixed disk to a reagent driving disk by a reagent moving mechanism
606 Confirmation process whether a vacant position presents in a fixed disk or not
607 Process for moving a reagent container to a reagent stand-by position by a reagent driving disk
608 Process for moving a reagent container to a loading system by a reagent driving disk
609 Analysis possible process Reference Numerals of the second embodiment according to the second aspect of the invention.

1 turntable
3 first partition
5 second partition
7 axis of rotation
9 compartments
11 reagent container assembly
13a, 13b, 13c container sections
15 welding spots
17 upper opening
19 cap
21 hinge 23 treatment zone
25, 27 compartment
29 container shift mechanism
31 treating means
33 frame
34 vertical pile
35 cantilever
37 stirrer
37, 39, 41 treatment units
39, 41 pipetting units
38 agitating means
40 pipetting means
43 linear horizontal guidance
44, 47, 49 driving means
53, 54 Catch springs
55, 56 compartment dividing walls
57 outer recess
62 shifting arm
63, 65 gripping or engagement elements
67 longitudinal axis
71, 77 driving means
73 horizontal guidance
75 driving means for rotating the shifting arm
79 photo-electric guards
85 drain channel Skilled artisans appreciate that elements in the figures are illustrated for simplicity and clarity and have not necessarily been drawn to scale. For example, the dimensions of some of the elements in the figures may be exaggerated relative to other elements to help improve understanding of the embodiment(s) of the present invention.

DETAILED DESCRIPTION

Embodiments of the present invention are described in detail below using the accompanying drawings. FIG. 1 is an exemplary configuration diagram of an automatic analyzer of the present invention, the analyzer including a reagent disk (also called turntable).

A samples transport line 114 in the automatic analyzer 101 transports samples 104 to sample dispensing pipettes neighboring a sample dispensing unit 115.

A sample dispensing tip/reaction vessel transport unit 106 is adapted to move above a reaction vessel disposal hole 102, a sample dispensing tip buffer 103, a reaction solution stirring unit 105, a sample dispensing tip/reaction vessel station 107, and part of an incubator disk 108, in directions of X-, Y-, and Z-axes. The sample dispensing tip/reaction vessel transport unit 106 moves reaction vessels from the sample dispensing tip/reaction vessel station 107 to the incubator disk 108. The sample dispensing tip/reaction vessel transport unit 106 also moves sample dispensing tips to the sample dispensing tip buffer 103. The sample dispensing unit 115 moves to an upper area of the sample dispensing tip buffer 103 having sample dispensing tips placed in the buffer, and picks up any one of the sample dispensing tips. Next after moving to an upper area of a sample and acquiring the sample by suction, the sample dispensing unit 115 further moves to an upper area of a reaction vessel on the incubator disk 108, and discharges the sample into the reaction vessel. After this, the sample dispensing unit 115 moves to an upper area of the sample dispensing tip/reaction vessel disposal hole and dumps the sample dispensing tip thereinto for disposal.

The incubator disk 108 has an ability to retain a plurality of reaction vessels, and moves each of the reaction vessels to a predetermined position on a circumference of the disk 108 by rotary motion.

The reagent disk 111 is adapted to retain a plurality of reagent containers 110, and moves each reagent containers 110 to a predetermined position on a circumference of the disk 111 by rotary motion. The reagent container 110 itself comprises multiple reagent included in a magnetic particles solution.

A reagent dispensing pipettor 109 moves to an upper area of a predetermined kind of reagent on the reagent disk 111, then suctions a predetermined amount of reagent, and after moving to an upper area of a predetermined reaction vessel on the incubator disk, discharges the reagent into the reaction vessel.

A magnetic particles stirring arm 116 (also called stirrer) as an agitating means is set on the reagent disk 111. The arm 116 moves to an upper area of the reagent container containing the reagent inclusive of the magnetic particles solution to be stirred, and stirs the magnetic particles solution by lowering a magnetic particles stirring element of the arm 116 and rotating the stirring element. In order to release the magnetic particles from a natural settling state in the solution, the magnetic particles stirring arm 116 stirs the magnetic particles immediately before the reagent is dispensed. After the stirring, the magnetic particles stirring arm 116 moves to an upper area of a cleaning cell containing a cleaning liquid, and then lowers and rotates the magnetic particles stirring element to remove sticking magnetic particles therefrom.

A reaction solution suction nozzle 112 suctions from the reaction vessel a reaction solution formed after an elapse of a predetermined reaction time from dispensing of a sample and the predetermined reagent, and then supplies the reaction solution to a detection unit 113. The detection unit 113 analyzes the reaction solution. The sample dispensing tip/reaction vessel transport unit 106 moves the analyzed reaction solution to the upper area of the sample dispensing tip/reaction vessel disposal hole and dumps the sample dispensing tip thereinto for disposal.

These actions of the apparatus are controlled by a host computer as a control means not shown.

The apparatus combines and repeats the above actions to efficiently analyze a plurality of samples over a plurality of analytical items.

Figure 2:
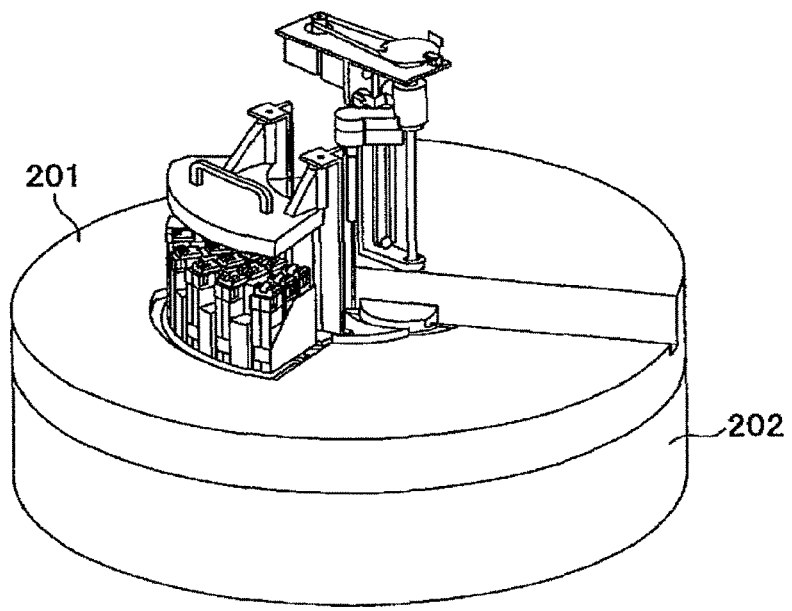
FIG. 2 is a perspective view of the reagent disk.

FIG. 2 is an external view of the reagent disk 111 according to the present invention. In order to control the reagent container 110 to a constant temperature, the reagent disk 111 includes a lid 201 having a heat-insulating function, and a jacket 202.

Figures 1, 3:
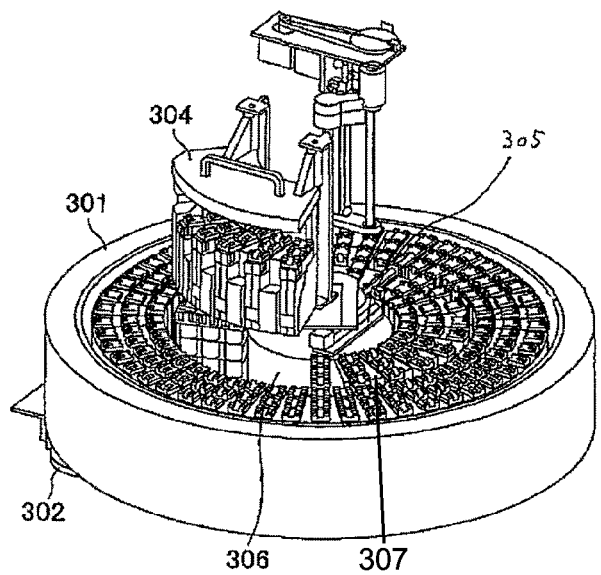
Figures 2, 3:
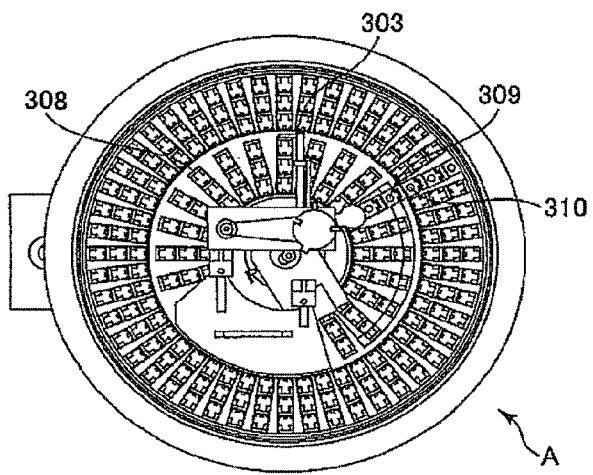
Figure 3:
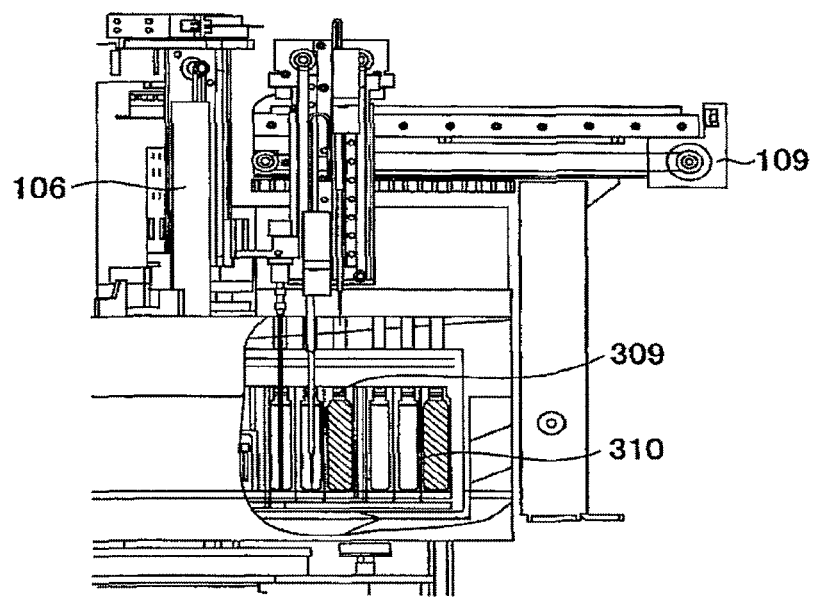

FIG. 3-1 is an external view of the reagent disk 111, showing the disk particularly with the lid 201 removed. The reagent disk 111 includes: a reagent driving disk 301 (also called first turntable partition) for transporting the reagent 110 to a desired position; a reagent driving disk driving unit 302 that drives the reagent driving disk 301; a fixed disk 303 (also called second turntable partition) adapted to make temporarily stand by thereon a reagent container that contains the reagent container 110 of the same kind; a loading system 304 that permits reagent containers 110 to be mounted in the system, even during analysis; a reagent container moving unit 305 (also called container shift mechanism) for moving the reagent container 110 from the reagent driving disk 301 to the fixed disk 303 or the loading system 304; a reagent information reading device 306 for reading information on the reagent, such as an analysis time and analytical items; and a partition plate 307 for partitioning a space between reagent containers 110.

FIG. 3-2 is a top view of the reagent disk shown in FIG. 3-1. The fixed disk 303 has a reagent stand-by position 308 and a reagent stirring position 309. In addition, a reagent dispensing position 310 is present on an operational path of the reagent driving disk 301. The reagent stirring position 309 is adjacent to the reagent dispensing position 310, and present on an operational path of the reagent dispensing pipettor. This region of the reagent disk is also called treatment zone.

FIG. 3-3 is a perspective view of the reagent disk shown in FIG. 3-2. While the magnetic particles stirring arm 116 is stirring the internal magnetic particles solution of the reagent container at the reagent stirring position 309, the reagent dispensing pipettor 109 can dispense the same kind of reagent into other reaction vessels. This ensures a sufficient magnetic-particles stirring time and enables simultaneous execution of dispensing and stirring. The same item can therefore be analyzed without reducing throughput. In FIG. 3-3, the reagent dispensing position 310 and the reagent stirring position 309 are lined up rectilinearly and both exist on the same position as the operational path of the reagent dispensing pipettor. Substantially the same also applies, even if the operational path of the reagent dispensing pipettor lies on a circumference.

A process flow of reagent container movement during reagent stirring is described below.

A position of a reagent container containing the reagent to be stirred is detected by the host computer. If this reagent container is present on the reagent driving disk, this disk moves to a position adjacent to the reagent stirring position, within an operational cycle time. Next, the reagent container moving unit moves the reagent container to the reagent stirring position within the fixed disk. Stirring by the magnetic particles stirring arm then follows.

If the reagent container is present in the reagent stand-by position, the reagent driving disk is checked for vacant positions. If a vacancy is present on the reagent driving disk, the reagent driving disk moves to a position adjacent to the reagent stand-by position in which the reagent container is present. Next, the reagent container moving unit moves the reagent container to the reagent driving disk and then as described above, further moves the reagent container to the reagent stirring position. Conversely if a vacancy is absent on the reagent driving disk, the host computer checks all reagent containers set on the reagent driving disk and searches for a reagent container temporarily movable to the reagent stand-by position. For example, the search is conducted using a parameter such as searching in ascending order of frequency of analytical request or in ascending order of frequency of measurement request. The reagent container, after being detected, is moved to the reagent stand-by position, and then the reagent container to be subjected to reagent stirring is moved to the reagent driving disk first and then to the reagent stirring position.

Figure 4:
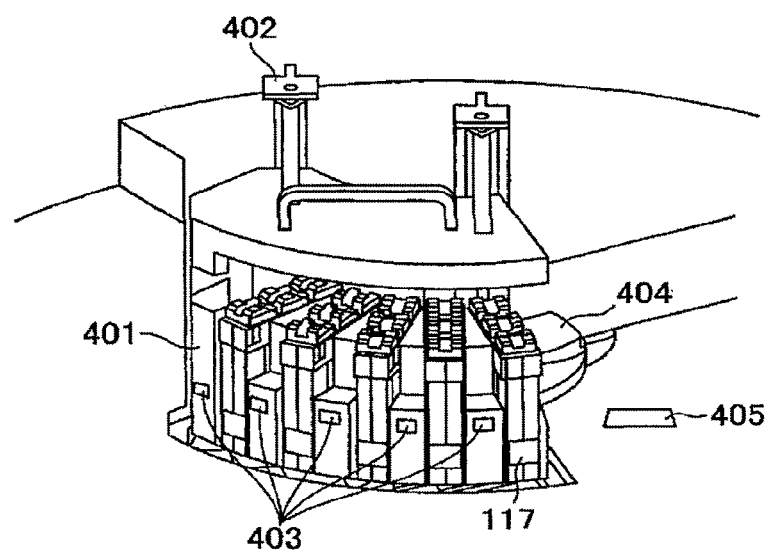
FIG. 4 is a schematic view of a loading system.

FIG. 4 is a schematic view of the loading system 205. The loading system forms part of the fixed disk located at an inner circumferential section of the reagent disk, and the system operates in upward and downward directions. For example, if the fixed disk exists at an outer circumferential section of the reagent disk, the loading system may be constructed so that the system can be pulled out in perpendicular or lateral directions. In addition, since a part of the fixed disk is the loading system and since the system has a shape that enables five reagent containers to be changed, two or more reagent containers would be replaceable or one reagent container would only be replaceable. The loading system 205 includes a reagent placing unit 401 in which to place reagent containers 110, a reagent actuator 402 adapted for upward/downward reagent actuation, indicators 403 each indicating whether the reagent is replaceable, a loading system locking unit 404 for locking the loading system, and an indicator lamp 405 notifying that the locking unit has unlocked the loading system. Among other methods useable to supply information on whether the loading system has been unlocked to enable reagent replacement would be one by providing a mechanism that slides the system upward to come out to the surface immediately after unlocking. Furthermore, although the loading system is constructed to be manually openable using a grip provided at the actuator, the system would be automatically movable to a reagent replacement position by, for example, adding a driving unit to the actuator itself.

An example of a reagent-adding sequence by an operator is described below.

A flow of successive reagent-loading operations is described first. The operator selects a reagent add/replace request via the host computer. The host computer analyzes a current operational status of the apparatus, then if reagent replacement is judged to be executable, activates the locking unit to unlock the loading system, and lights up the indicator lamp to notify that the reagent replacement can be conducted. Pursuant to the information from both the host computer and the indicator lamp, the operator judges that the reagent is replaceable. After confirming that the reagent replacement is executable, the operator opens the loading system, then loads a replacement reagent container into a vacant position, and closes the loading system. After the closing of the loading system following completion of replacement reagent container mounting, the operator checks a sensor or the like and makes sure that the loading system is properly closed.

Next, a flow of successive reagent-replacing operations is described below. The operator selects a reagent add/replace request via the host computer, as in the reagent-adding sequence. The host computer then analyzes the current apparatus status. After judging reagent replacement to be executable, the host computer unlocks the loading system by the locking unit to enable the replacement. Since the loading system is also used as the fixed disk, all reagent containers may have already been mounted in the system when the replacement is conducted. In such a case, the indicator indicates whether the reagent container is replaceable. For example, if the indicator has a red and a green light source and the red one is on, the corresponding reagent container is unusable as a replacement, and if the green light source is on, the reagent container is usable as a replacement. Alternatively, if the reagent container cannot be used as a replacement, providing the locking unit properly will prevent the particular reagent container from being pulled out for removal. After replacing the reagent container, the operator closes the loading system properly and then confirms through the host computer that the loading system has been properly closed. The confirmation completes the replacement sequence.

Figure 5:
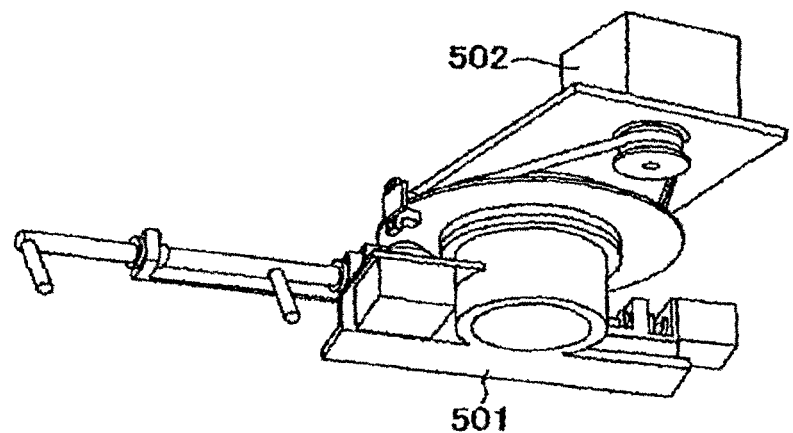
FIG. 5 is a schematic view of a reagent container moving unit.
Figures 1, 5:
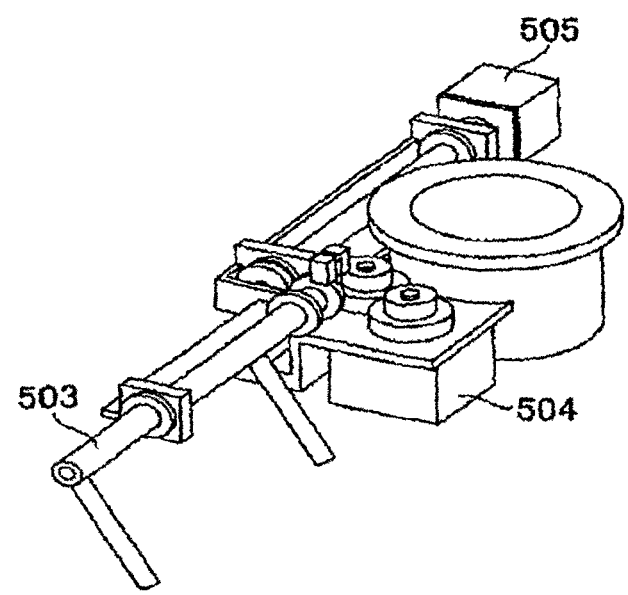

FIG. 5 is a schematic view of the reagent containers moving unit 305 (also called container shift mechanism). The reagent container moving unit 305 includes an arm mechanism 501 that moves a reagent container 110, and a drive portion 502 that rotates the arm mechanism 501. FIG. 5-1 is a schematic view of the arm mechanism 501. The arm mechanism 501 includes an arm 503 used for moving the reagent container 110, a lateral arm drive portion 504 that moves the arm forward and backward, and a rotational arm drive portion 505 that rotates the arm. The reagent container moving unit 206 moves reagent containers between the loading system and the reagent driving disk, as well as between the reagent driving disk and the fixed disk. A reagent container moving sequence is described below using an example of a movement between the reagent driving disk and the fixed disk. First, the reagent driving disk moves a desired reagent container to a position in the same radial direction as that of the fixed disk onto which the reagent container is to be stored. After the movement, the arm mechanism rotates to a position to which the reagent container can be moved. Next, the lateral arm drive and the rotational arm drive operate for the arm to grip the reagent container, and then the lateral arm drive operates to make the arm move the gripped reagent container from the reagent driving disk to the fixed disk. Finally, the lateral arm drive and the rotational arm drive cause the arm to release the container from the gripped position. This completes the moving sequence. When the arm grips the reagent container, an actuator such as a motor may actuate the arm to hold the container from both sides, for example. In addition, when the reagent container moving unit moves the reagent container, the arm may be driven by the actuator to grip the container or pressed against the container, to conduct the movement.

Figure 6:
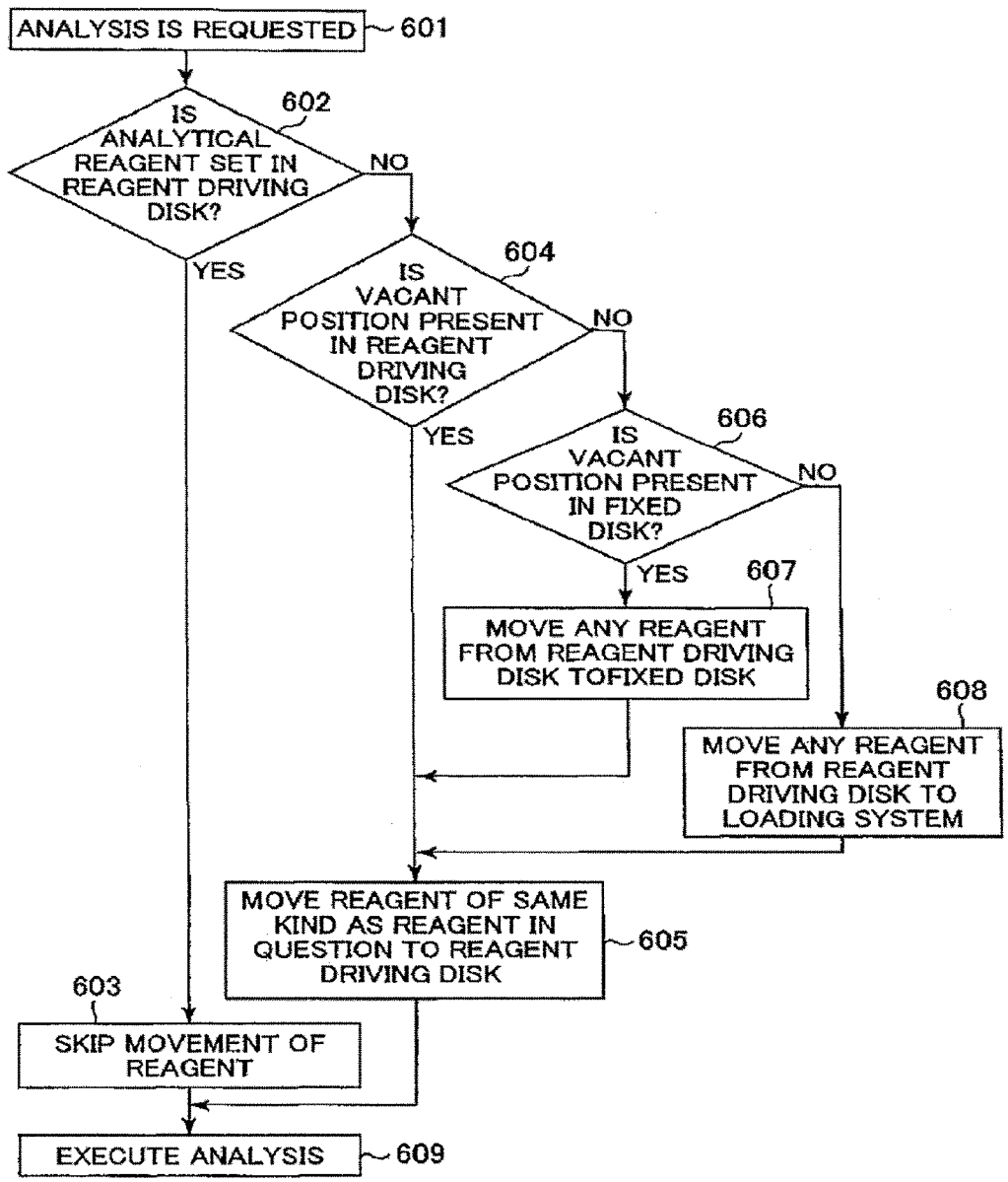
FIG. 6 is a flow diagram of a reagent container moving operations.

FIG. 6 is a flow chart that shows the flow of analytical reagent container movement on the reagent disk of the present invention. When analysis is requested from the operator in step 601, whether a reagent container to be used for the analysis exists on the reagent driving disk is next confirmed in step 602. If the reagent container to be used for the analysis is already set on the reagent driving disk, a process for no reagent container movement is executed in step 603 and the analysis is immediately executed in step 609. If the reagent container to be used for the analysis is not set on the reagent driving disk, any reagent container containing the same kind of reagent as used for the analysis is moved from the fixed disk to the reagent driving disk. Prior to this movement, it is confirmed in step 604 whether a vacant position is present on the reagent driving disk. If a vacant position is present, the reagent container moving unit moves any reagent container containing the same kind of reagent, from the fixed disk to the reagent driving disk, in step 605. If a vacant position is absent, whether a vacant position exists on the fixed disk is confirmed in step 606. If a vacant position on the fixed disk is exists, a reagent container movable to the reagent fixed position is moved from the reagent driving disk to the reagent fixed position in the moving process step 607. If a vacancy is absent, the reagent container moving unit moves any reagent container containing the same kind of reagent, from the reagent driving disk to the loading system, in step 608. After this movement, the same kind of reagent container required for the analysis is moved from the fixed disk to the reagent driving disk in step 605 by the reagent container moving unit, and then in step 609, an executable state of the analysis is registered in the host computer.

An installation flow of the reagent disk can be divided into two major sequences: (1) a sequence from completion of reagent container loading to a start of the analysis, and (2) a sequence for reagent replacement due to a shortage or expiration of the reagent.

(1) Sequence from completion of reagent container loading to a start of the analysis. An example of a sequence from completion of reagent container loading to a start of the analysis is described below. After a reagent container containing the required kind of reagent has been loaded from the loading system, the host computer upon confirming that the loading system has been closed properly by the operator activates the locking unit to lock the system, and reads reagent information from the mounted reagent container using a reagent information reading device equipped in or on the disk. The reagent container has an identifier affixed thereto. Measurement items and other information are pre-written on the identifier. The identifier is, for example, a bar code, a radio-frequency identification (RFID) tag, or the like. The reagent information, when read properly, will be registered and the reagent container moved to the reagent driving disk by the reagent container moving unit. The host computer will recognize a position on the reagent driving disk where the moved reagent container was loaded, and register the information. The movement will be followed by a process required for the analysis, such as calibration. The reagent container upon completion of this process will be usable, and the host computer will register the reagent as one that can be used for the analysis.

(2) Sequence for reagent replacement due to a shortage or expiration of the reagent. An example of this sequence is described below. The host computer measures the amount of reagent in the reagent container. The reagent information that has been registered in the loading system contains an expiration date of the reagent, and the host computer judges from this date whether the reagent maintains its chemical effectiveness. If the reagent has already expired or is insufficient in quantity, the host computer will deliver an alarm to the operator, notifying that the reagent requires replacement. At the same time, the reagent container moving unit will move the reagent container from the reagent driving disk to the loading system. At this time, the host computer will confirm the reagent container information registered in the loading system. If the loading system is now capable of accepting a plurality of reagent containers and has at least one vacant loading position, the particular reagent container will be moved to one of the vacancies. If the loading system has no vacancy, the reagent container will be moved to the fixed disk and made to stand by thereon until a vacant loading position has been created. After the reagent container has stood by, when the vacancy occurs in the loading system, the reagent driving disk and the reagent container moving unit will operate to move a replacement reagent container to the loading position. After the movement of the replacement reagent container, the host computer will notify to the operator that the reagent container has become ready for the replacement.

With regard to FIGS. 7-15 a further embodiment of the invention is described below.

The turntable shown in FIG. 7 has a circular construction with a radially outer ring-shaped first partition 3 and a radially inner circular or ring-shaped second partition 5. The first turntable partition 3 is movable about a vertical central axis of rotation 7 relative to the second turntable partition 5. The first turntable partition 3 and the second turntable partition 5 of the embodiment according to FIGS. 7-15 correspond essentially to the reagent driving disk 301 and the fixed disk 303, respectively of the first embodiment according to FIGS. 1-6.

The first turntable partition 3 is equipped with a plurality of compartments 9, namely forty-eight compartments in the present embodiment. The compartments 9 are separated by dividing walls 56. Each compartment 9 is adapted to accommodate a reagent container assembly 11 in a fitted position.

Figures 9A, 9B, 10:
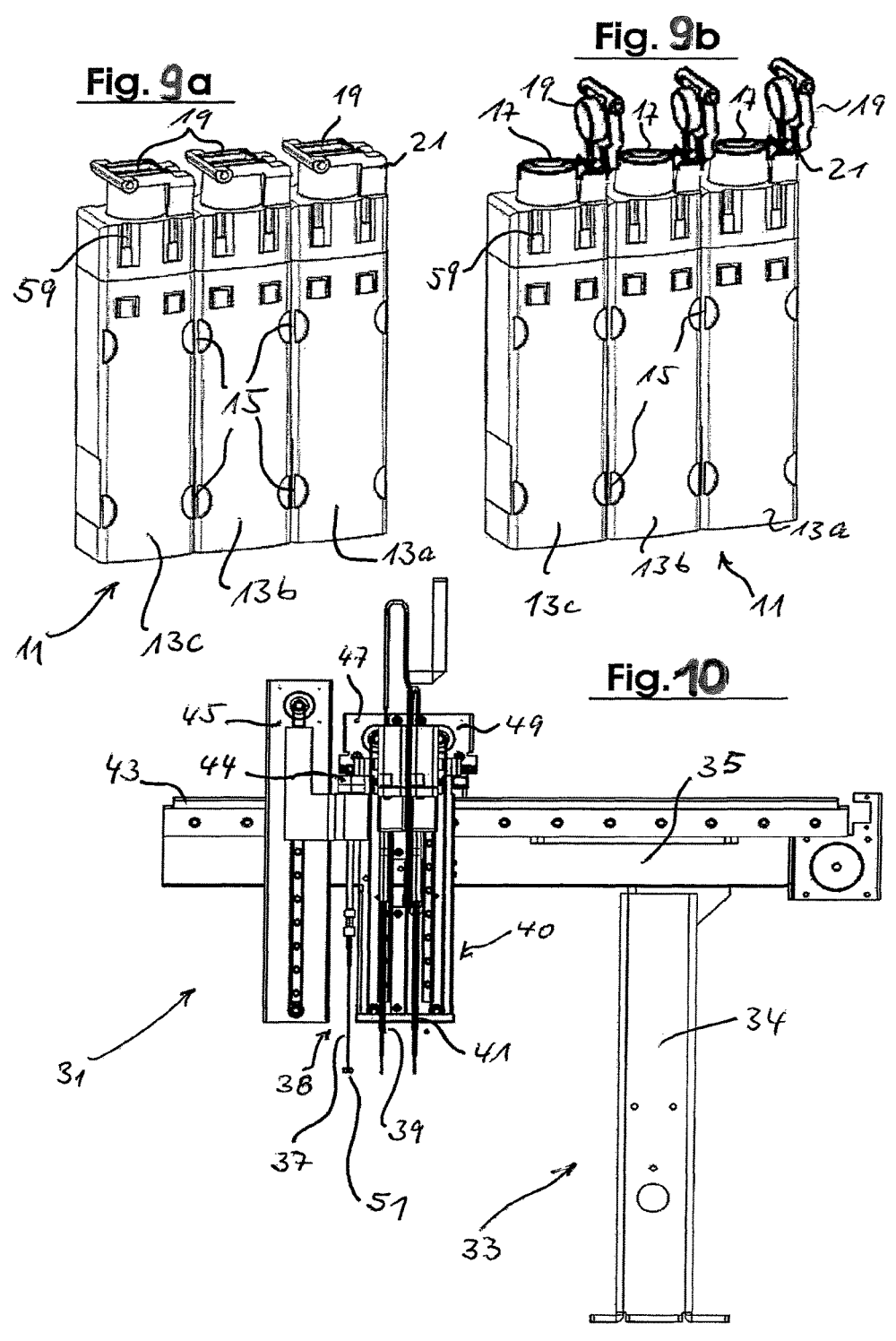

Each reagent container assembly 11 consists of three containers or container sections 13a, 13b, 13c as shown in FIGS. 9a and 9b. The containers 13a, 13b, 13c are made of plastic material and are interconnected and fixed to each other at welding spots 15 so that they form a reagent container assembly 11 with three container sections 13a, 13b, 13c in an in-line configuration. Each container section 13a, 13b, 13c contains a particular reagent to be used in particular analytical determinations to be performed by means of the analyzer comprising the turntable 1. In the present embodiment the outer container section 13a in FIGS. 9a and 9b contains a suspension of microparticles ("beads") which are used in the analytical determinations as micro carriers for complex molecules which are characteristic for the analysis.

The other container sections 13b and 13c contain other specific reagents to be used in analysis steps according to a specific assay protocol.

Each container section has an upper opening 17 which is normally closed by means of a cap 19 as shown in FIG. 9a. Each cap 19 is pivotable mounted to the housing of its container section 13a, 13b, 13c so that it is pivotable about the hinge 21 between a closing position according to FIG. 9a and the opening position according to FIG. 9b. Normally, the container sections 13a, 13b, 13c are closed by said caps 19 being in the closing position, in order to avoid evaporation of the reagents contained therein.

The container sections 13a-13c have to be opened according to FIG. 9b if access to the inner volume thereof is required. An automatic cap manipulating mechanism (not shown) is adapted to selectively open or close the container sections 13a-13c by moving the caps 19 in the respective closing or opening positions. Said cap manipulating mechanism is provided in a treatment zone 23 for treating a reagent container assembly 11 stored on said turntable 1 in respective compartments 9 and 25. The compartments 9 are arranged side-by-side to form an arcuate or ring-shaped row of compartments 9 on the first turntable partition 3. The second turntable partition 5 has a first compartment 25 which is radially aligned in the treatment zone 23. The compartments 25, 27 of the second turntable partition 5 are open at their radially outer ends, whereas the compartments 9 of the first turntable partition 3 are open at their radially inner ends. Since the second turntable partition 5 is fix with regard to the axis of rotation 7, the first compartment 25 remains in the treatment zone 23. Since the first turntable partition 3 is rotatable around the second partition 5 each compartment 9 of the second turntable partition 3 can be selectively moved into the treatment zone 23 in radial alignment with the first compartment 25 of the second turntable partition 5 in a mutual transfer position as it is shown in the snap shot of FIG. 7 for the compartment 9a of the first turntable partition 3. In said mutual transfer position the container assembly 11 which occupies the first compartment 25 can be shifted radially outward into the compartment 9a of the first turntable partition. Thereafter said reagent container assembly 11 can be removed from the treatment zone 23 by rotation of the first turntable partition 3. The first compartment 25 of the second turntable partition 5 is then vacant and may be loaded with another reagent container assembly 11 from the first turntable partition 3 after having positioned that reagent container assembly 11 in radial alignment with the first compartment 25.

Beside the first compartment 25 are arranged some further compartments 27 on the second turntable partition 5 to form a circular arc shaped row of radially oriented compartments 25, 27. Each compartment 27 may be used to exchange a reagent container assembly 11 between the first turntable partition 3 and the second turntable partition 5 in the manner as described above with regard to the first compartment 25.

The radial shifting of reagent container assemblies 11 between the turntable partitions 3, 5 is performed automatically by means of a container shift mechanism 29.

FIG. 8 shows the turntable 1 in the same top plan view as FIG. 7, but with further components of the apparatus for providing reagents, namely treating means 31 for treating reagent container assemblies 11 positioned in said treatment zone 23.

The further treatment means 37 are also shown in a side view in FIG. 10. They comprise a frame 33 in the shape of a gallows with a vertical pile 34 fixed radially outward of the turntable 1 and a cantilever 35 extending horizontally from said pile 33 above the turntable 1 so as to dispose treatment units 37, 39, 41 for acting in said treatment zone 23. The treatment unit 37 is a stirrer which is a part of an agitating means 38 that is guided for horizontal movement on a linear guidance 43 which is attached to the cantilever 35. The units 39, 41 are pipetting tubes of a pipetting means 40 which is also guided for horizontal movement on said linear guidance 43. The agitating means 38 and the pipetting means 40 are movable independently from each other along the guidance 43 by driving means which are controlled by a control means (not shown).

The agitating means 38 has a vertical driving means 45 for selectively lowering or raising the stirrer 37, and a driver 44 for rotating the stirrer 37.

The pipetting means 40 comprises vertical driving means 47, 49 for each pipette unit 39, 41. Said vertical driving means 47, 49 of the pipetting units 39, 41 are controllable by the control means in order to independently raise or lower the pipetting units 39, 41.

Figure 11:
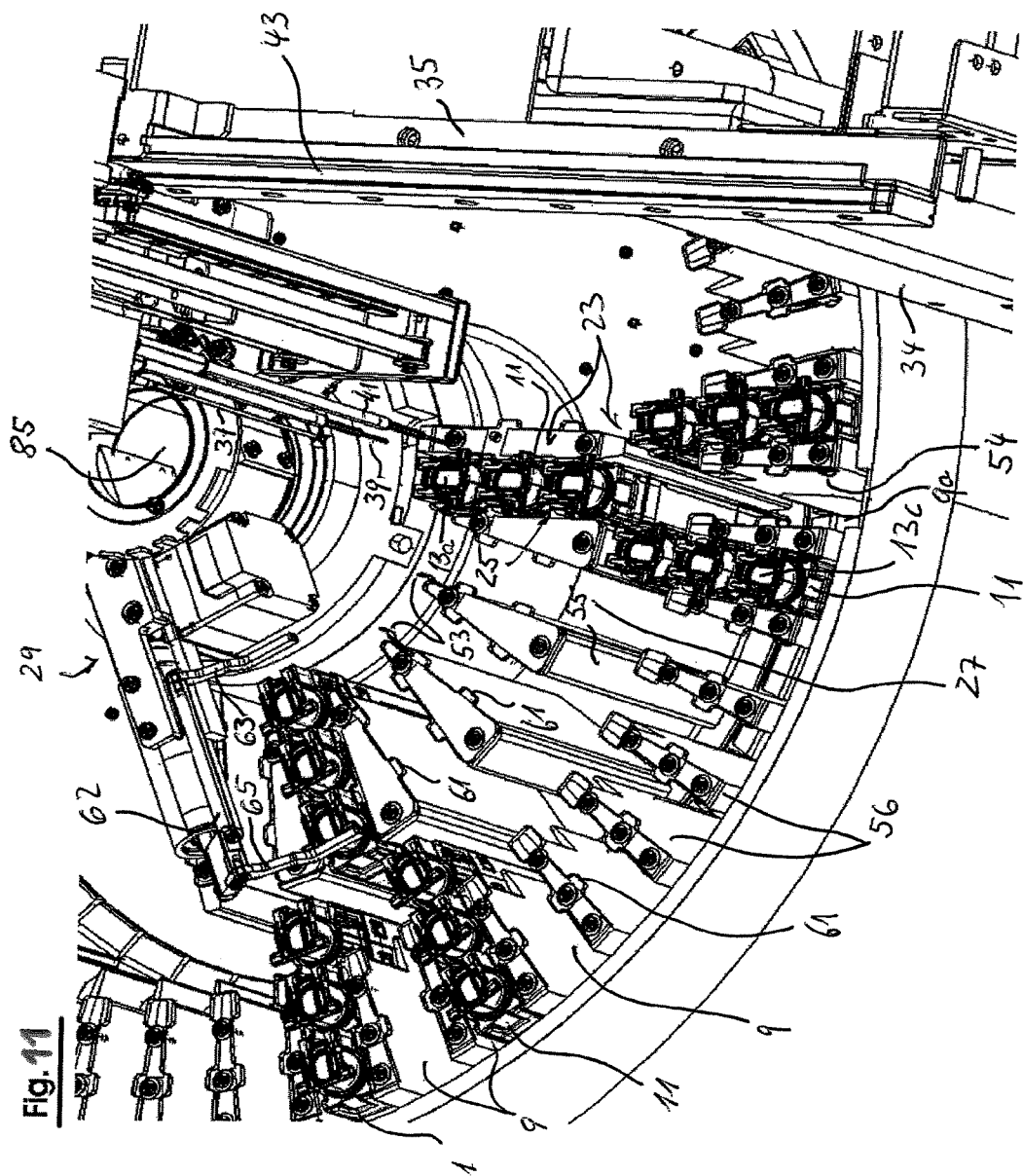
FIG. 11 is a perspective view of the treatment zone of the apparatus of FIG. 8.
Figure 12:
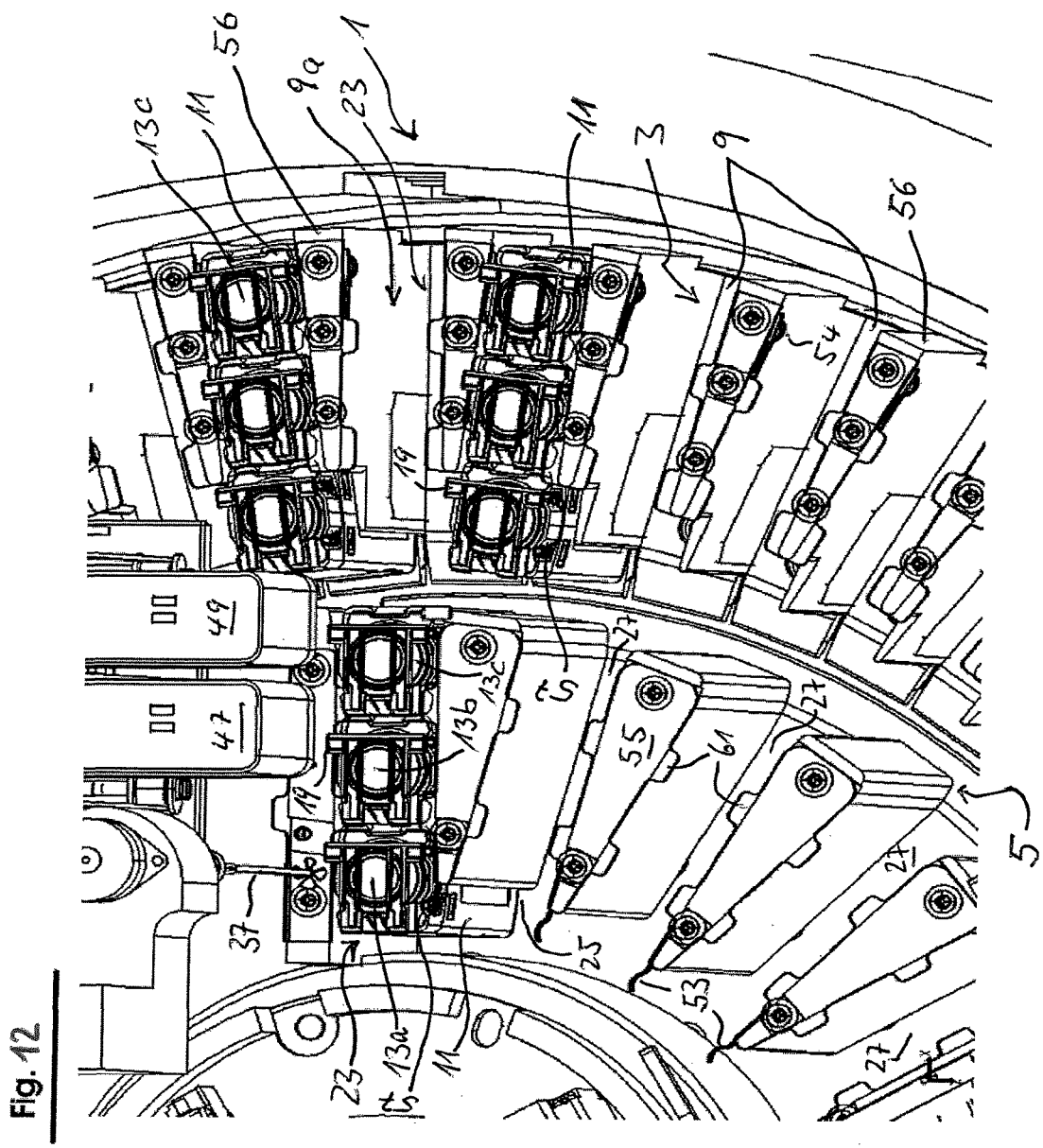
FIG. 12 is a perspective view of a detail of the treatment zone.
Figure 13:
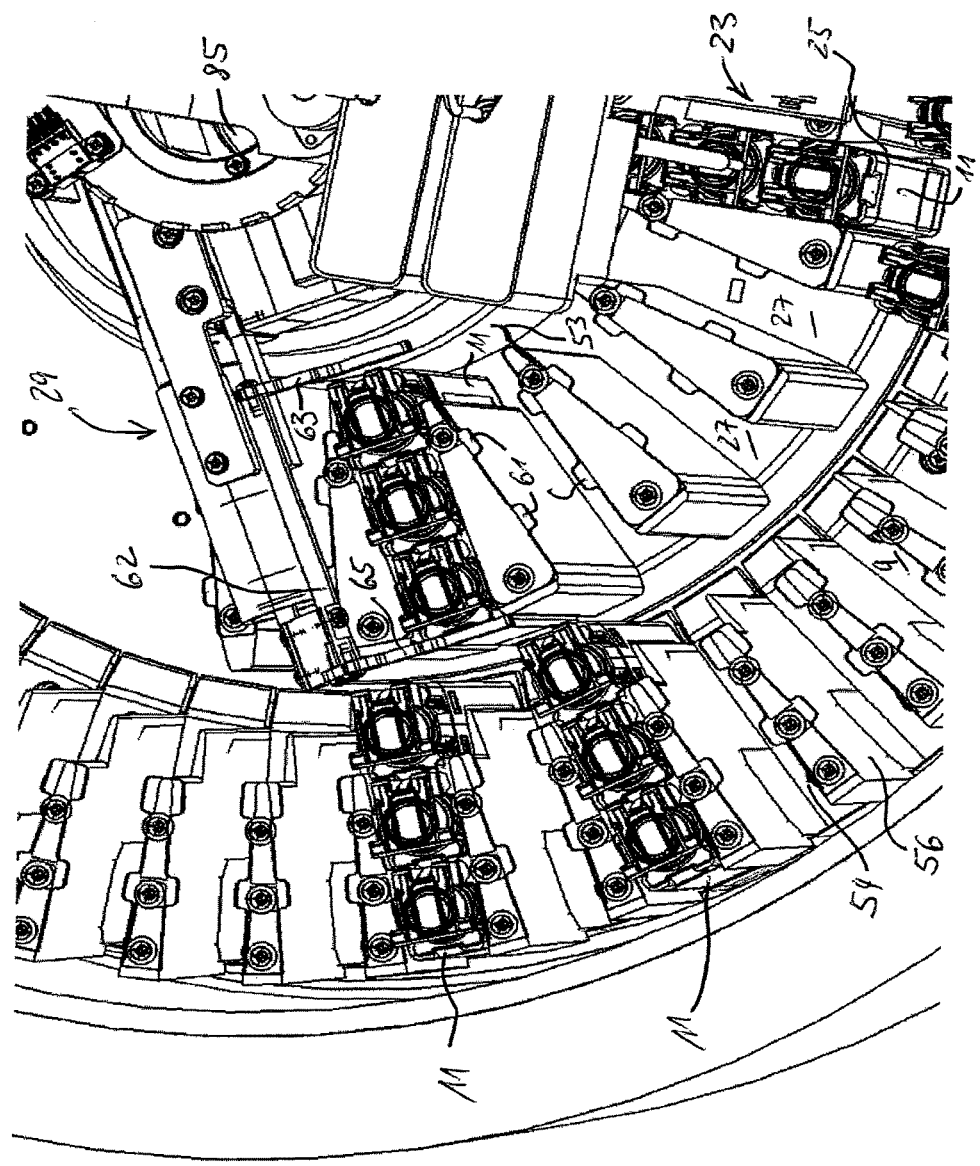
FIG. 13 is a perspective view of a detail of the turntable and the container shift mechanism.

In FIG. 8 the agitating means 38 are adjusted on the horizontal guidance 43 and in stand-by position in which the stirrer 37 is in vertical alignment with the radially innermost disposed container section 13a of a reagent container assembly 11 accommodated in the first compartment 25 (cf., FIG. 7 and FIG. 11). Before the agitating means 38 are activated to mix the content of said container section 13a in the first compartment 25, the cap manipulating means has to be activated to move the cap 19 of this container section 13a in the opening position (cf., FIG. 9b). Then the vertical drive means 45 may be activated to lower the stirrer 37 so as to insert said stirrer 37 through the uncovered opening 17 into the inner volume of the container section 13a, in order to agitate the reagent contained therein. The rotation of the propeller 51 of the stirrer 37 about its vertical axis is controllable by the control means.

As mentioned above, the container section 13a contains a bead suspension which must be homogenized by mixing before it is extracted by a pipetting unit 39, 41 for use in an analysis step. This step of agitating the suspension of beads is also called a bead mixing step. The bead mixing step is usually more time consuming then pipetting steps of the pipetting means 40. For this reason the apparatus for providing reagents according to FIG. 8 will be operated in such a manner that each bead mixing operation will be performed on the second turntable partition 5 with the container section 13a of the particular reagent container assembly 11 is positioned on the radial innermost location of the first compartment 25.

During the bead mixing step the first turntable partition 3 may be driven by its drive means to rotate in order to adjust a reagent container assembly 11 in a predetermined position in the treatment zone 23. Also the pipetting means 40 may be operated during the bead mixing step is performed. The pipetting means 40 is used to extract reagents from reagent container assemblies 11 currently adjusted in the treatment zone 23. The pipetting means 40 may be moved along its horizontal guidance 43 to selectively access in the treatment zone 23 container sections 13a, 13b, 13c in the first compartment 25 of the second turntable partition 5 or container sections 13a, 13b, 13c of a
reagent container assembly 11 in a respective compartment 9a of the first turntable partition 3. After the current bead mixing step has been terminated and the stirrer 37 has been retracted from the container section 13a of the respective reagent container assembly 11 in the first compartment 25, this reagent container assembly 11 may be transferred to the first turntable partition 3 by radially shifting the reagent container assembly 11 outwards into a vacant compartment of the first turntable partition 3 by means of the container shift mechanism 29.

It is to be noted that at the same time both radially aligned compartments 9a, 25 in the treatment zone 23 may be occupied by a respective reagent container assembly 11, and that during the stirrer 37 of the agitating means 38 is activated to mix the content of container section 13a of the reagent container assembly 11 in the compartment 25 of the second turntable partition 5, the pipetting means 40 may be used to extract reagents from container sections 13a, 13b, 13c of the reagent container assembly 11 in the compartment 9a of the first turntable partition 3.

Catch springs 53, 54 are provided as snapping means on the vertical compartment dividing walls 55, 56. The catch springs 53 are mounted at an upper and radial inner position to the compartment dividing walls 55 of the second turntable partition 5 so as to be able to snap in an outer recess 57 of the radially innermost positioned container section 13a of a reagent container assembly 11 accommodated in the first compartment 25. The reagent container assembly 11 is automatically or self-adjusted when the catch spring has entered the radially innermost vertical groove or recess 57 of said reagent container assembly 11.

The catch springs 54 are mounted at an upper and radially outer position to the vertical compartment dividing walls 56 of the first turntable partition 3 in order to snap in a respective groove shaped recess 59 of the reagent container assembly 11 accommodated in the respective compartment 9 of the first turntable partition 3. Instead of the catch springs other snap means may be provided for adjusting the reagent container assemblies 11 in compartments 9, 25, 27.

Figure 15:
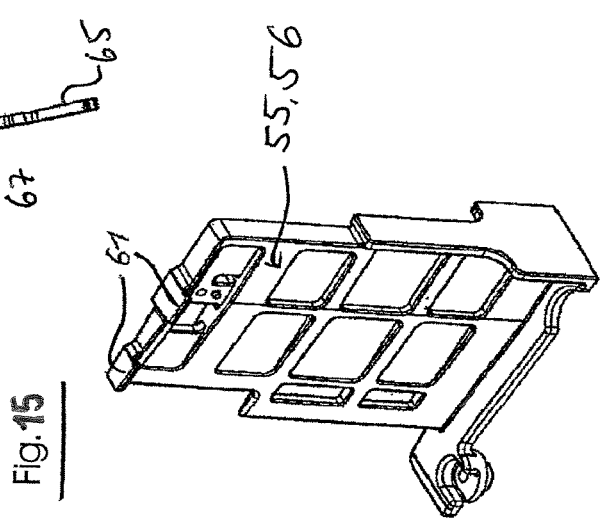
FIG. 15 is a perspective view of an alternative embodiment of a compartment dividing wall.

The compartments 9, 25, 27 may be equipped with spring-loaded bottom elements (not shown) which are adapted to urge the reagent container assemblies 11 accommodated in the compartments 9, 25, 27 upwardly against upper stops 61 extending from the compartment dividing walls 55, 56. The reagent container assemblies 11 are adjusted precisely also in the vertical direction by this measure. The upper stops 61 are shown in FIGS. 7-13 as sidewardly extending protrusions of sheets mounted on top of the compartment dividing walls 55, 56 by means of screws. According to an alternative embodiment of the walls 55, 56 as shown in FIG. 15 the stops 61 may be integrated parts of the walls 55, 56, wherein the walls 55, 56 with integrated stops are preferably plastic parts or milled metal parts.

The container shifting mechanism 29 has a shifting arm 62 with two gripping or engagement elements 63, 65 which are pivotable about the longitudinal axis 67 of the shifting arm 62 between an engagement position and a release position. The gripping elements 63 and 65, respectively, may engage a reagent container assembly 11 at an upper part at respective longitudinal ends thereof. The point of engagement is preferably located at a low level in the upper half of a respective reagent container assembly 11. The radial distance between said gripping elements 63, 65 is a little bit greater than the length of the reagent container assemblies 11 so that the gripping elements 63, 65 can adopt a reagent container assembly 11 therebetween. By shifting the shifting arm 62 in its longitudinal direction a reagent container assembly 11, that is adopted between the gripping elements 63, 65 in their engagement position, can be transferred between respectively aligned compartments of the first turntable partition 3 and the second turntable partition 5. The container shift mechanism 29 is movable to rotate the shifting arm 62 about the axis of rotation 7 to selectively gain access to each compartment 25, 27 of the second turntable partition 5 in order to transfer reagent container assemblies 11 from each compartment 25, 27 of the second turntable partition 5 to a respective aligned compartment of the first turntable partition 3. According to one embodiment the pivot movement of the elements 63, 65 may be started during the rotation of the shifting arm 62 about the axis 7.

When the gripping elements 63, 65 are in their release position they do not interfere with reagent container assemblies 11 on the turntable 1, so that the shifting arm 62 can not move a reagent container assembly 11.

It is to be noted that the container shifting mechanism 29 with its gripping elements 63, 65 can be operated to hold a reagent container assembly 11 in position in a respective compartment 9, 25, 27, e.g., during the opening of the container sections 13a-13c of that reagent container assembly 11 by means of the automatic cap manipulating mechanism.

Figure 14:
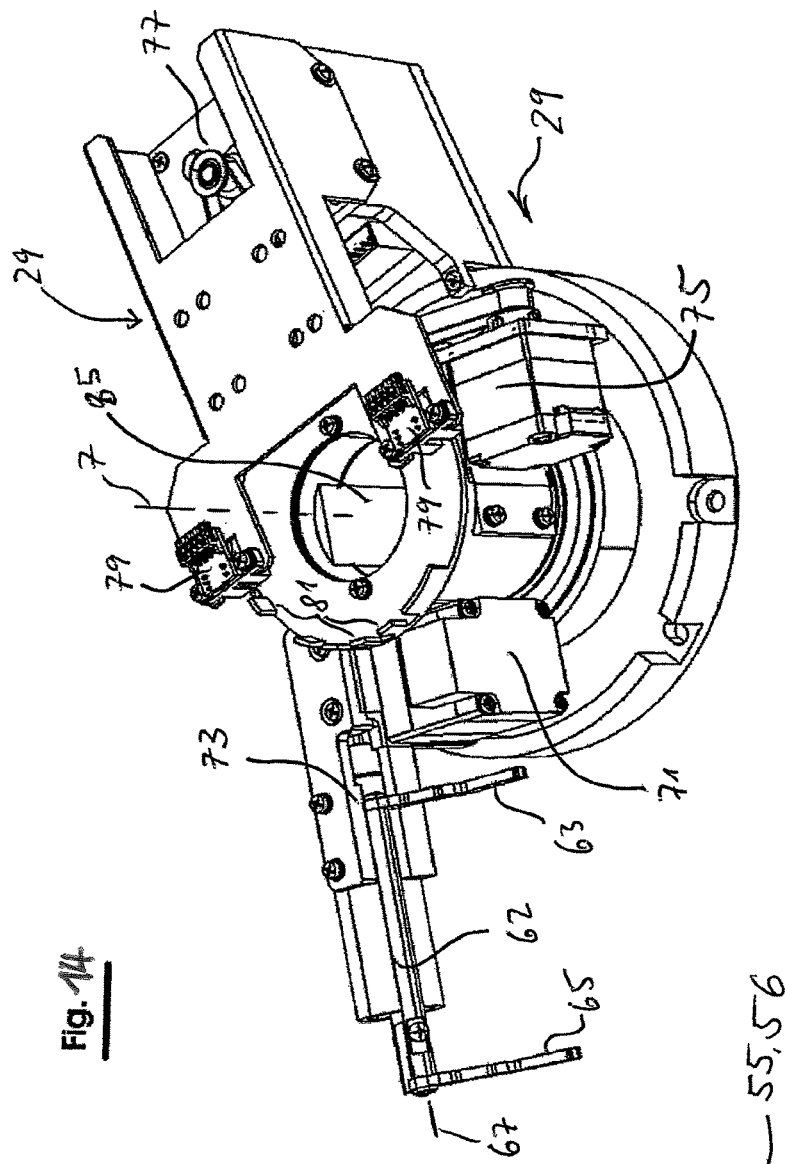
FIG. 14 is a perspective view of the container shift mechanism.

In the perspective view of the container shifting mechanism in FIG. 14 reference number 71 denotes a drive means for shifting the shifting arm 62 along a horizontal guidance 73 in its longitudinal direction. The reference number 75 denotes a driving means for rotating the shifting arm 62 about its longitudinal axis 67 in order to pivot the gripping elements 63, 65 between their engagement position and release position.

Reference number 77 in FIG. 14 denotes a driving means for rotating the container shift mechanism 29 about the vertical axis of rotation 7. The angular positions of the container shifting mechanism 29 relative to the axis of rotation 7 are monitored by means of photo-electric guards 79 which act together with a pattern of merlons 81 distributed on a circular arc around the axis of rotation 7.

In a similar manner the shift position and the pivot position of the shifting arm 62 are monitored by photo-electric guards.

The turntable 1 has arranged at its center a vertical tube, e.g., a hollow shaft which forms a drain channel 85 for draining a cleaning fluid of a cleaning station adapted for cleaning the stirrer 37 of the agitating means 38. For this reason, the agitating means 38 is movable along its horizontal guidance 43 between the stand-by position shown in FIG. 8 and a cleaning position in alignment with the drain channel or tube 85. Usually a cleaning step of the stirrer 37 is required after each bead mixing step. The provision of the cleaning station in the central region of the turntable is a space-saving measure which avoids long ways between the stand-by position and the cleaning position of the stirrer 37.

There are also provided cleaning means for cleaning the pipetting tubes 39, 41. The latter cleaning means are positioned outside the turntable 1 and are not shown.

According to the present invention it is possible to perform more time-consuming treatment steps on the second turntable partition 5 while faster treatment steps, including the rotation of the first turntable partition 1 and pipetting operations of the pipetting units 39, 41, may be performed. The apparatus for providing reagents according to the present invention may be operated very efficiently to achieve a high throughput of the analyzer. As mentioned above the control means is programmed to control the operation of the apparatus for providing reagents according to the particular program for performing a lot of analytical determinations by means of the analyzer.

It is to be noted that the movements of the reagent container assemblies 11 on the turntable 1, i.e., rotation of the turntable 1 in both rotational directions and the shifting of the reagent container assemblies 11 between the turntable partitions 3 and 5 should be performed without abrupt starts and stops in order to avoid an intensive sloshing of the reagents in the reagent container assemblies 11. Therefore, the controlling means is programmed to control the driving means of the turntable 1 so as to perform the movements of the reagent container assemblies 11 in a harmonic manner. The same applies to the movement of the shift mechanism 29.

Also the course of movement of the treatment means 38 and 40 is controlled according to a particular scheme in order to achieve a trouble-free and time-optimized operation of the apparatus for providing reagents.

It is to be noted that in principle all features of the first aspect of the invention may be realized in an analyzer according to the second aspect of the invention and vice versa.

It is noted that terms like "preferably", "commonly", and "typically" are not utilized herein to limit the scope of the claimed subject matter or to imply that certain features are critical, essential, or even important to the structure or function of the embodiments disclosed herein. Rather, these terms are merely intended to highlight alternative or additional features that may or may not be utilized in a particular embodiment of the present invention.

It is also noted that the terms "substantially" and "about" may be utilized herein to represent the inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

It will be apparent to those skilled in the art that various modifications and variations can be made to the embodiments described herein without departing from the spirit and scope of the claimed subject matter. Thus it is intended that the specification cover the modifications and variations of the various embodiments described herein provided such modifications and variations come within the scope of the appended claims and their equivalents.

The invention claimed is:

1. A method for providing reagents within an analyzer comprising:
providing:
a turntable having an axis of rotation and configured to store thereon a plurality of reagent container assemblies in an arrangement of at least one arcuate row, wherein each of the plurality of reagent container assemblies has at least two container sections, each of which has an inner volume to contain a particular reagent, and which container sections are arranged side-by-side in a row on a straight radial line and are connected to form a unitary cassette type assembly;
at least one treatment zone for treating reagent container assemblies stored on the turntable, the treatment zone is defined within the circumference of the turntable and has a surface area less than the surface area of the turntable;
treatment means comprising pipetting means and agitating means, where the treatment means treat reagent container assemblies positioned in the treatment zone, and the pipetting means and the agitating means are movable along a rectilinear operational path that extends within the circumference of the turntable, wherein the treatment zone is radially aligned with the rectilinear operational path of the pipetting means and the agitating means, and the treatment zone has a surface area less than the surface area of the turntable;
wherein the turntable comprises compartments arranged to accommodate the reagent container assemblies at predetermined locations on the turntable so as to form the arrangement of at least one arcuate row of reagent container assemblies corresponding to the arrangement of the compartments;
a circular first turntable partition that is adjustable by rotation so as to selectively move respective ones of the compartments in predetermined positions for disposing reagent container assemblies in predetermined positions in and out of the treatment zone and the first turntable partition is centered around the axis of rotation and carrying the arcuate row of compartments;
a fixed second turntable partition arranged radially adjacent to the first turntable partition and carrying a first compartment for accommodating a reagent container assembly therein, wherein the second turntable partition is fixed without a motor and is incapable of rotation with respect to the axis of rotation such that the first compartment remains located in the treatment zone;
the first turntable partition is rotatable relative to the fixed second turntable partition about the axis of rotation so as to selectively adjust a compartment of the first turntable partition in radial alignment with the first compartment of the fixed second turntable partition in a mutual transfer position in which a reagent container assembly is radially shiftable by a container shift mechanism between the aligned compartments in the treatment zone, the container shift mechanism comprising a shifting arm extending out from the axis of rotation and comprising a gripping element rotatable about a longitudinal axis of the shifting arm between an engagement position and a release position;
the pipetting means is movable along the rectilinear operational path to access at least one of reagent container assemblies positioned in a predetermined position in the treatment zone;
the agitating means is movable along the rectilinear operational path and configured to access in the treatment zone a reagent container assembly accommodated in the first compartment of the fixed second turntable partition in order to agitate a content of the container assembly in the first compartment; and
the first turntable partition is operable to provide reagent container assemblies in the treatment zone for being treated by the pipetting means independently of the operation of the agitating means and out of the treatment zone by rotation; and rotating the gripping element about the longitudinal axis of the shifting arm.

2. The method according to claim 1, further comprising arranging the first circular turntable partition radially outward of the second turntable partition with regard to the axis of rotation.

3. The method according to claim 1, further comprising rotating a second gripping element about the longitudinal axis of the shifting arm between the engagement position and the release position, the second gripping element located between the first gripping element and the axis of rotation along the arm.

4. The method according to claim 3, further comprising simultaneously operating the container shift mechanism and the pipetting means in order to simultaneously treat separate reagent container assemblies with the container shift mechanism and the pipetting means.

5. The method according to claim 1, wherein the second turntable partition carries a plurality of compartments including the first compartment for accommodating reagent container assemblies in an arrangement of an arcuate row radially adjacent the arcuate row of compartments of the first turntable partition, and further comprising radially aligning the second turntable partition with respective compartments of the first turntable partition in mutual transfer positions.

6. The method according to claim 3, further comprising moving the container shift mechanism around the axis of rotation at selected angular positions corresponding to angular positions of the radial alignment of compartments aligned in their mutual transfer positions.

7. The method according to claim 1, further comprising aligning at least one of the compartments of the first turntable partition and at least one of the compartments of the second turntable partition to dispose reagent container assemblies contained therein on a straight radial line when positioned relative to each other in the predetermined positions in the treatment zone, and wherein the apparatus for providing reagents further comprises a driving and guiding means for selectively moving the pipetting means to reagent container assemblies positioned relative to each other in the predetermined positions in the treatment zone.

8. The method according to claim 7, wherein the pipetting means comprise at least two pipetting units and, moving each pipetting unit according to a specific treatment program via the driving and guiding means.

9. The method according to claim 1, further comprising simultaneously operating the agitating means and the pipetting means to simultaneously treat separate reagent container assemblies.

10. The method according to claim 1, wherein the turntable has a radial inner center including the axis of rotation, and further providing a cleaning station for cleaning treatment means and a drain channel for draining cleaning fluid, and wherein the drain channel is arranged in the area of the radial inner center, between three separate driving means of the container shift mechanism, each of the driving means providing movement for an aspect of the container shift mechanism along a different direction, and further comprising draining the cleaning fluid.

11. The method according to claim 10, further comprising moving the agitator means between a working position to agitate fluid in a reagent container assembly positioned in the first compartment and at least one other position outside of the container assembly.

12. The method according to claim 1, further comprising moving the pipetting means and agitating means independently from each other along the rectilinear operational path.

13. The method according to claim 1, wherein the treatment means comprises a frame fixed radially outward of the turntable and which extends above the turntable, and further comprising moveably disposing the pipetting means and agitating means for movement along the rectilinear operational path and acting in the treatment zone.

14. The method according to claim 1, wherein the treatment means comprises a frame fixed radially outward of the turntable and which extends horizontally above the turntable via a cantilever, the cantilever moveably disposed thereon the pipetting means and agitating means for movement along the rectilinear operational path and acting in the treatment zone, and further comprising independently moving the pipetting means and agitating means along the cantilever.

15. The method of claim 1 further comprising shifting the shifting arm longitudinally along a horizontal guidance via a drive means.

\* \* \* \* \*